United States Patent [19]
Ivey

[11] Patent Number: 5,605,537
[45] Date of Patent: Feb. 25, 1997

[54] ENDOSCOPIC DEVICE

[76] Inventor: Jack L. Ivey, 1900 Preston Rd. #350, Plano, Tex. 75093

[21] Appl. No.: 287,044

[22] Filed: Aug. 8, 1994

[51] Int. Cl.$^6$ .................................................. A61M 1/30
[52] U.S. Cl. ............................................. 604/21; 604/27
[58] Field of Search ....................... 604/22, 27, 51, 604/164, 167, 169, 170, 173, 256, 96; 128/4

[56]  References Cited

U.S. PATENT DOCUMENTS

| | | |
|---|---|---|
| 1,531,213 | 3/1925 | Nimmer . |
| 2,568,566 | 9/1951 | Sokolik . |
| 3,308,825 | 3/1967 | Cruse . |
| 3,426,759 | 2/1969 | Smith . |
| 3,753,439 | 8/1973 | Brugarolas et al. . |
| 3,810,471 | 5/1974 | Truhan . |
| 4,068,664 | 1/1978 | Sharp et al. . |
| 4,451,257 | 5/1984 | Atchley . |
| 4,487,600 | 12/1984 | Brownlie et al. . |
| 4,535,773 | 8/1985 | Yoon . |
| 4,750,902 | 6/1988 | Wuchinich et al. . |
| 4,767,404 | 8/1988 | Renton . |
| 4,828,550 | 5/1989 | Kurimoto . |
| 5,098,387 | 3/1992 | Weist et al. ............................ 604/153 |
| 5,146,925 | 9/1992 | Snow .................................... 128/658 |
| 5,186,714 | 2/1993 | Boudreault et al. . |
| 5,205,816 | 4/1993 | Dodson et al. . |
| 5,207,213 | 5/1993 | Auhll et al. ................................ 128/6 |
| 5,241,990 | 9/1993 | Cook .............................. 137/625.46 |
| 5,242,387 | 9/1993 | Loughlin . |
| 5,247,966 | 9/1993 | Stevens et al. .................. 137/625.69 |
| 5,263,928 | 11/1993 | Trauthen et al. . |
| 5,372,587 | 12/1994 | Hammerslag et al. . |

*Primary Examiner*—Randall L. Green
*Assistant Examiner*—Perry E. Van Over
*Attorney, Agent, or Firm*—Larry L. Uland

[57]  ABSTRACT

A multifunctional device for use in endoscopic medical procedures, capable of suction, irrigation and aqua-dissection, comprising an elongated tube that is open at both ends, a pair of valves in communication with the tube such that the device may be used for either suction, irrigation, or aqua-dissection, and further having an optional shield which may be attached for the suctioning of large volumes of fluid therethrough. A removable seal is attached to the proximal end of the tube, which seal can be replaced with an optional end cap for allowing the tube to be used to transmit other instruments into the operative field, which other instruments can be used simultaneously with the device while the device is performing suction or irrigation.

19 Claims, 1 Drawing Sheet

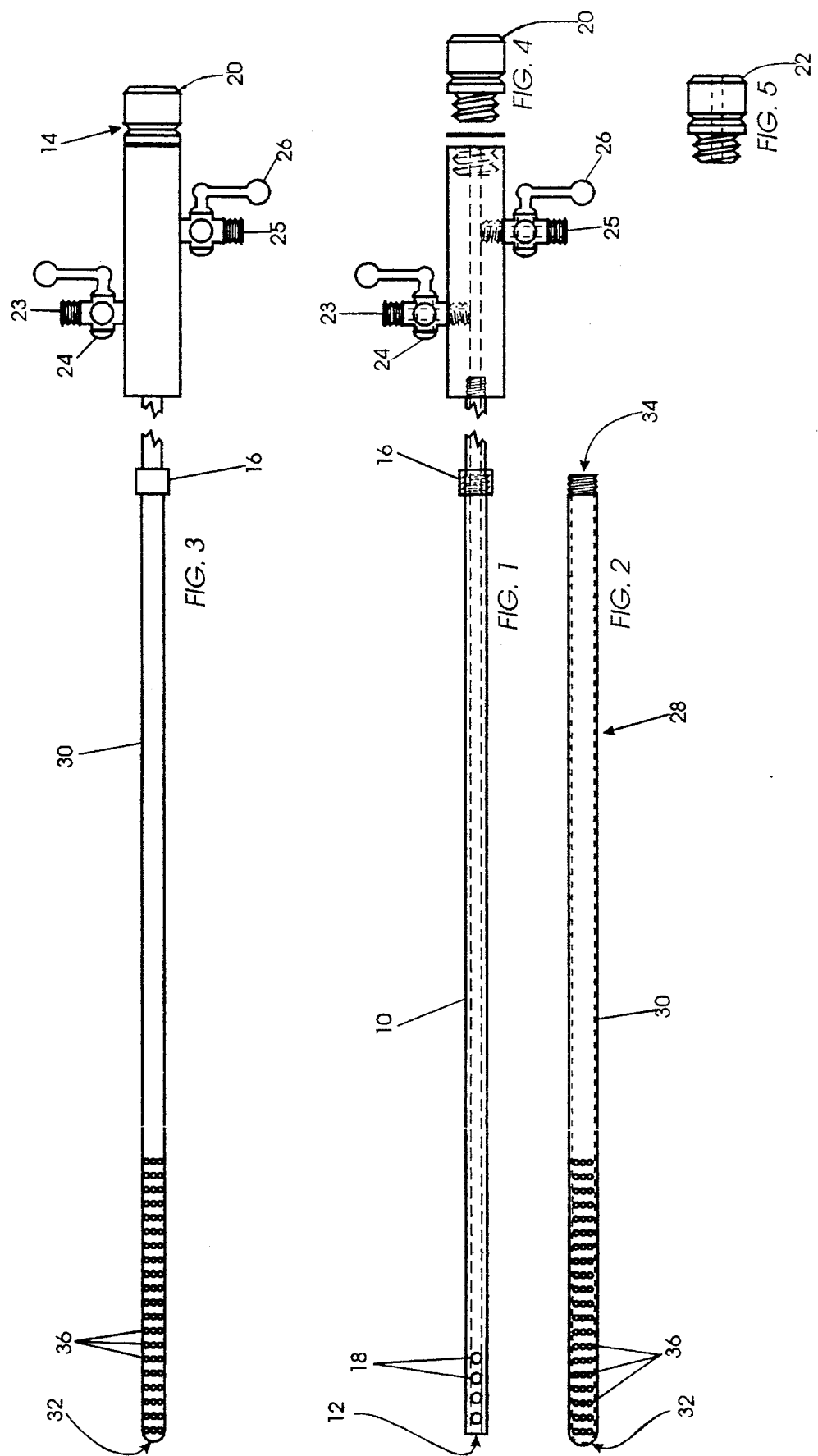

ENDOSCOPIC DEVICE

BACKGROUND OF THE INVENTION

Endoscopic surgery has revolutionized a number of surgical procedures in specific areas of the body. Endoscopic surgery is surgery that is performed by inserting surgical instruments into the body through relatively small incisions, with the surgeon observing his own actions on a video monitor. The video camera, lighting, and all instruments that enter the body are operated by the surgeon from outside the body. Endoscopic techniques offer many advantages: they can be performed as outpatient surgical procedures; they typically entail shorter patient recovery time and less pain; and, they are more economical because there is less of the patient's time lost from work. Even in endoscopic procedures, however, both pain and recovery time increase when more instruments have to be inserted and removed during the procedures. Hence, it is desirable to limit the total number of separate devices that have to be inserted and removed.

Body fluids are present in the operative field during endoscopic procedures, just as with any other type of surgery. These body fluids can inhibit the view of the camera and prevent the surgeon from seeing clearly what he is doing. The surgeon's view may also be obscured by other fluids which may be introduced into the operative field as part of the procedure, such as with irrigation or aqua-dissection. As a sponge cannot be used in endoscopic procedures, suction devices must be used. These suction devices are generally some type of elongated tube attached to a source of vacuum, and are most commonly inserted into the body through an incision separate from that required for other surgical instruments. It is also necessary to irrigate the operative field during endoscopic procedures. This is usually accomplished by inserting into the body through yet another incision another tube attached to a source of saline solution or other irrigation fluid. Subsequently, irrigation fluids which are used must be suctioned back out.

Aqua-dissection is another procedure that is sometimes used in endoscopic surgeries. In aqua-dissection, irrigation fluid under pressure is injected into the body to break up areas of scar tissue or adhesions. Instillation of fluids under pressure creates cleavage planes which the surgeon can then lyse by sharp dissection. This procedure compensates for the general inability to use blunt dissection during operative endoscopy. Aqua-dissection also results in large volumes of irrigation fluids being instilled into the body, which fluids must then be suctioned out of the body so that the surgeon can see.

It is also sometimes necessary to place additional lighting, fiberoptic cameras, lasers or other devices into the operative field, all of which must be inserted through additional incisions, which results in increased pain and recovery time for the patient.

A problem with the current endoscopic suction devices on the market is that most of them are open-ended tubes that can become inadvertently suctioned onto body structures such as bowels or fallopian tubes. This not only blocks the removal of fluid, but can also cause injury. Such inadvertent suctioning onto body structures also requires the stoppage of surgery while the vacuum source is shut off and the suction device is released from the structure to which it is attached. When suctioning large volumes of fluids, these suction devices often become clogged with blood clots and other debris, which further precipitates the need for stopping the surgery and removing such debris.

Another problem with many suction devices of the prior art is that they use trumpet valves which can be clogged easily with blood clots and other debris. Again, when blockages occur at such valves, surgery must be stopped while the problem is corrected. Presently, hospitals charge approximately $3,400.00 for the first two hours of surgery, and charge an additional approximate amount of $1,200.00 for each hour thereafter. Difficult endoscopic cases may last as long as between 4 and 6 hours. It is readily apparent that decreasing operating room time can result in tremendous health care cost savings.

It may be readily observed, that a significant disadvantage of endoscopic suction and irrigation devices of the prior art, is that such devices do not typically allow for the seal-tight insertion of additional instruments, other than the endoscopic suction and irrigation devices, into the same tube used for suction and irrigation. Such disadvantage commonly prevents the use of the additional inserted instruments simultaneously with the use of irrigation or vacuum.

Devices for providing suction or irrigation have been used in surgery for many years, as can be seen by the following examples of the prior art. U.S. Pat. No. 1,531,213 by Nimmer discloses a tubular syringe designed only for injecting fluids in one of two selectable directions out of a shielded tube: It should be noted, that the Nimmer device is capable neither of performing suctioning procedures, nor of allowing for the seal-tight insertion of other instruments through the tube portion of the device. U.S. Pat. No. 2,568,566 by Sokolik discloses a suction and irrigation device comprising a two-way elongated cylindrical syringe connectable to a triple ported cross-head fitting, which fitting connects the syringe simultaneously to both a fluid-feeding inlet tube and a fluid-withdrawing outlet tube. The outer surface of the syringe of Sokolik further comprises a plurality of longitudinally extending corrugations or ridges divided by a plurality of longitudinally extending fluid collection channels, in an alternating radial arrangement. Each of the ridges contains an internal fluid feeding conduit which is open at a top end where it is in communication with the cross-head fitting and closed at a bottom end. A large central fluid withdrawing conduit is axially formed in the syringe, and is surrounded by the fluid feeding conduits and fluid collection channels. The fluid withdrawing conduit is also open at a top end where it is also in communication with the cross-head fitting and includes a small withdrawing orifice at a bottom end for withdrawing fluid from the bottom of a body cavity. The fluid withdrawing conduit further has a cross sectional area which corresponds to the combined cross sectional areas of the fluid feeding conduits. A plurality of inlet orifices is further provided on the inner edges of each ridge for spraying flushing fluid from the fluid feeding conduit within the ridge and into the fluid collection channels located on either side of the ridge. A similar plurality of outlet orifices is provided in the apex of each fluid collection channel for communicating between the collection channel and the fluid withdrawing conduit. Although the Sokolik device does provide for the simultaneous suction and irrigation of fluids, and further provides a novel method of solving the problem of bodily organs adhering to suction orifices, it does not allow for the seal-tight insertion of other instruments through either the cross-head fitting or the syringe portion of the device while simultaneously using such instruments with suction or irrigation. Furthermore, the design of the Sokolik device makes its production cost prohibitive when compared to the simple and economical design of the present invention.

U.S. Pat. No. 3,308,825 by Cruse discloses a suction device designed to overcome the tendency of suction devices to adhere to soft tissues via the provision of an outer tube member adjoined to the open end of a suction tube and including a plurality of annular ribs defining an external groove which is in communication with the interior of the tube member through a plurality of tube side ports. As well as failing to provide irrigation means, the Cruse device includes disadvantages which are similar to those displayed by the device of Sokolik: it does not allow for the simultaneous seal-tight insertion and use of other instruments through the tube portion of the device, and its design makes its production cost prohibitive when compared to the simple and economical design of the present invention.

U.S. Pat. No. 4,451,257 by Atchley discloses a surgical aspirator or suction device having a single poppet valve connected to an elongated aspirator tube and an outer similarly elongated shield surrounding the aspirator tube, and having a plurality of perforations and a squared off distal end. Unfortunately, this device cannot be used for both suction and irrigation. Also, the shape of the aspirator tube and shield would be inappropriate for most endoscopic surgery procedures. Further more, additional instruments cannot be inserted through the aspirator tube of the Atchley device for simultaneous use with the aspirator tube.

U.S. Pat. No. 4,487,600 by Brownlie et al. discloses a suction device that has an adjustable flow rate and a plurality of longitudinally spaced radial apertures adjacent to its free end, through which fluids may be suctioned. U.S. Pat. No. 4,767,404 by Renton discloses another suction device with a plurality of perforations for preventing the inadvertent attachment of the device to soft tissue. Neither the device of Brownlie et al., nor that of Renton is designed for the simultaneous seal-tight insertion and use of other instruments through the tube portion of the device.

U.S. Pat. No. 5,186,714 by Boudreault et al. discloses a multifunctional surgical device comprising a pistol-grip shaped holder that can be attached to various elongated instruments. One such instrument is a combination suction/irrigation device, with includes a plurality of orifices at its distal end. The handle of this device can also be attached to a cannula which can be used for inserting other instruments such as lasers, fiberoptics, etc., into the surgical area. However, these additional instruments cannot be introduced through the suction/irrigation tube of the Boudreault et al. device or used simultaneously with the suction/irrigation tube. Hence, when the surgeon wishes to use these other instruments, he must remove the suction/irrigation tube from the patient, disassemble the device, then reassemble it replacing the suction/irrigation tube, and insert the reconfigured device into the body of the patient. Thus, when compared to the operative procedure available through use of the present invention, any operative procedure using the device of Boudreault et al. and involving the use of a plurality of other surgical instruments would increase significantly both the time required to perform such procedure and the amount of pain and recovery time experienced by the patient. Also, the use of a pistol shaped handle for holding the operative instruments, as disclosed by Boudreault et al., would tend to reduce significantly the tactile sensitivity afforded to the surgeon through the instrument. A still further disadvantage of the teaching of Boudreault et al. is that the suction/irrigation device of said teaching fails to include effective and economical means for preventing adhesion of body members to the suction orifices.

U.S. Pat. No. 5,205,816 by Dodson et al. discloses a laparascopic device for suction, irrigation and blunt dissection. Blunt dissection is the parting of tissue by pushing it apart, as opposed to cutting or aqua-dissection. Similar to other endoscopic suction and irrigation devices of the prior art, this device has no accommodation for reducing clogging or sticking when suctioning, and also fails to include accommodation for the insertion of other instruments through the body of the device.

U.S. Pat. No. 5,241,990 by Cook discloses another basic suction/irrigation device and valving system which includes disadvantages of the prior art which have been already enumerated concerning other devices. This system does not include an optional shield for preventing the adhesion of body members to the suction device, or any means of inserting additional instruments through the body of the device for simultaneous use with the suction or irrigation means of the device.

U.S. Pat. No. 5,242,387 by Loughlin discloses a suction/irrigation device that includes a suction shield. The shield is a second body that fits over two separate tubes used to provide irrigation and suction means. The shield has a hemispherical dome at one end with a plurality of small orifices communicating with the interior of the shield, for allowing suction and irrigation in the operative field without clogging or suctioning onto a vital organ. However, those skilled in the art will recognize that the Loughlin instrument as designed cannot be used in the operative field without the shield, and hence cannot be used for aqua-dissection as can the present invention. Furthermore, other instruments such as monopolar knives or fiberoptic devices have to be inserted into the operative field separately from the Loughlin device and thus cause an increased amount of pain and recovery time when compared with the results available through using the present invention.

SUMMARY OF THE INVENTION

The invention comprises a combination suction/irrigation/aqua-dissection device having an optional suction shield and a removable end-cap or seal. Said device includes an elongated hollow tube having a distal end (for extending into the operative field in a patient's body), a proximal end (for extending outside a patient's body such that it can be manipulated by the surgeon) and a substantially cylindrical side wall. Both ends of the tube are open. There are a plurality of ports formed in the tube side wall near the distal end for communicating with the interior of a patient's body. Near the proximal end of the tube are an irrigation conduit and a vacuum conduit, each including a valve for regulating the communication between the interior of the tube and a source of irrigation or vacuum may be connected to said conduit. These valves further allow the same tube to be used for suction, irrigation or aqua-dissection, without having to insert additional instruments. The proximal end of the tube is covered with an end cap or seal. When the end cap is used, rather than the seal, it has an opening of sufficient size for allowing the insertion of another device such as a monopolar knife or fiberoptic laser into and through the end cap and tube, wherein such another device can be used simultaneously with irrigation or suctioning procedures incorporating the tube.

A sealable shield securing structure circumscribes the outside of the tube at a position located near the proximal end, but between the distal end and the suction and irrigation valves. An optional suction shield is also provided, for preventing the adhesion of body members to the open tube distal end or to the ports near the tube distal end. Said suction shield comprises another larger elongated hollow tube with a distal end and a proximal end, the distal end being closed and of hemispherical shape, having a plurality of ports formed in the shield hollow tube and located near the shield distal end for communicating with the interior of the shield. The proximal end of the shield is threadably connectable to the shield securing structure so that, when desired, the shield may be attached to the tube for allowing the suction of large volumes of fluid without incurring the risk of clogging or suctioning onto anatomical structures such as fallopian tubes or bowels.

The above and other features of the invention, including various and novel details of construction and combinations of parts, will now be more particularly described with reference to the accompanying drawings. These together with other objects of the invention, along with the various features of novelty which characterize the endoscopic device of the present invention, are pointed out with particularity in the claims appended hereto and forming part of this disclosure. The more important objects of the present invention have been outlined rather broadly in order that the detailed description thereof which follows may be better understood, and in order that the present contribution to the art may be better appreciated. For a better understanding of the instant invention, its operational advantages and the specific objects attained by its uses, reference should be made to the accompanying drawings and descriptive matter in which there are illustrated various embodiments of the invention.

Those versed in the art will readily ascertain, however, that the present invention is capable of other embodiments and of being practiced and carried out in various other ways. In this respect, the details of construction disclosed herein, including the component materials and the arrangements of the components set forth in the following description and appended drawings, are for illustrative purposes, only, and are not intended to be limiting in scope. Those skilled in the art will appreciate, as well, that the conception upon which this disclosure is founded, may be readily utilized as a basis for the designing of other structures, methods, and systems for carrying out the several purposes of the present invention. Said other structures may include, but are not limited to, those which are aesthetic in nature, or those which include the substitution of other materials as they become available, and which substantially perform the same function in substantially the same manner with substantially the same result as the present invention. It is important, therefore, that the claims appended hereto be regarded as including such equivalent materials, structures, constructions, methods, and systems insofar as these do not depart from the spirit and scope of the present invention.

BRIEF DESCRIPTION OF THE DRAWINGS

FIG. 1 is a plan view of an endoscopic device embodying features of the present invention.

FIG. 2 is a plan view of a suction shield embodying features of the present invention.

FIG. 3 is a plan view of an endoscopic device with a shield attached and embodying features of the present invention.

FIG. 4 is a plan view of a seal for use with the endoscopic device of the present invention.

FIG. 5 is a plan view of an optional end cap for use with the endoscopic device of the present invention.

DETAILED DESCRIPTION

Referring to FIG. 1, the preferred embodiment of the endoscopic device of the invention includes an elongated hollow endoscopic tube 10 having a distal end 12 and a proximal end 14, both ends of the tube 10 being open. In the preferred embodiment, the overall length of the tube 10 is 30 cm, though other lengths are acceptable depending on the anticipated use.

A sealable shield securing structure 16 circumscribes the outside of the tube 10 at a position preferably located nearer the tube 10 proximal end 14, though said sealable shield securing structure 16 can be placed almost anywhere on the tube 10. However, in the preferred embodiment, the shield securing structure 16 is located 13 cm from the proximal end 14 and 17 cm from the distal end 12.

From the distal end 12 of the tube 10 to the sealing structure 16, the external diameter of the tube 10 in the preferred embodiment is 3 mm. This section of the tube 10 is also preferentially made of a corrosion resistant material, such as titanium. From the shield securing structure 16 to the proximal end 14 of the tube 10, the external diameter of the tube 10 in the preferred embodiment is 5 mm, and this section of the tube 10 may be made of the same material used in the distal end 12 section, or of some other material. In the preferred embodiment, the entire device is made of titanium.

Further provided in the tube 10 are a plurality of ports 18 in the side of the tube 10 near the distal end 12, for allowing communication between the interior of a patient's body and the interior of the tube 10. In the preferred embodiment, the ports 18 are approximately 1.2 mm in diameter and are arranged in rows and columns around the tube 10, such that the columns are uniformly distributed about the tube 10, each column extending linearly and parallel to the axis of the tube 10. It is still further preferred that the ports 18 are spaced at regular intervals within each column, at an easily renderable distance, such as 2.5 mm apart. By such a distribution of the ports 18, lengths and depths may be accurately determined in the surgical arena, using the tube 10 as a ruler. In the preferred embodiment, there are two columns and four rows.

The proximal end 14 of the tube 10 is open, and the opening is covered with a seal 20. (See FIG. 4.) The seal 20 provides a removable means for sealing the proximal end 14 of the tube 10, so that the device may be used for irrigation and suction without leakage at the proximal end 14. In the preferred embodiment, the seal 20 is made of an elastic material, such as rubber, that can be stretched over the proximal end 14 of the tube 10. The seal 20 may also be made of hard materials such as metals, and attach to the tube 10 by complimentary threads. Another means of covering the proximal end 14 opening would be to have a cork inserted into the proximal end 14 of the tube 10. Those skilled in the art will recognize a number of other ways for sealing the proximal end 14 with a removable seal or fitting for allowing the proximal end 14 to be selectively sealed or opened in accordance with the present invention.

For example, the seal 20 can be replaced with a end cap 22 (FIG. 5) that has an opening of sufficient size to allow for the insertion of another device, such as a monopolar knife, fiberoptic laser, fiberoptic camera, lighting, etc., through the end cap 22 and down the length of the tube 10. In the preferred embodiment, the end cap 22 is also made out of rubber, though it could be made also out of metal, and used either with or without a gasket (not shown). The use of a rubber end cap 22, or of gasketed materials with a metal cap 22, provides a leakproof seal between the end cap 22 and an instrument inserted through the end cap 22 and down the length of the tube 10; and, thereby, allowing the simultaneous use of suction or irrigation through the tube 10 with the use of such an instrument. The leakproof seal of the end cap 22 may also be accomplished by having an internal fitting (not shown) placed in the proximal end 14. However the leakproof seal is accomplished, the provision of such a seal affords a surgeon the ability to insert additional instruments into the surgical arena while simultaneously using the device for suction and irrigation.

Near the proximal end 14 of the tube 10 are two conduits (an irrigation conduit 23 and a vacuum conduit 25) which are each connected to the tube 10 at a conduit first end and are in communication with the tube 10 interior. Affixed to the irrigation conduit 23 and the vacuum conduit 25 are valves 24 and 26, respectively, for regulating the communication between the interior of the tube 10 and sources of suction or irrigation which may be connected to a second end of the respective conduit 23 or 25. The valves 24 and 26 allow the same device to be used for suction, irrigation or aqua-dissection, without requiring the cumbersome and time-consuming insertion of additional instruments. The valves 24 and 26 should be of a style that is difficult to clog, such as gate valves. To further prevent clogging, the valves should have as large an internal diameter as is practical, which preferably is as large as the internal diameter of the tube 10. The valves 24 and 26 are preferably located at varying distances from the proximal end 14 of the tube 10, for allowing the surgeon to differentiate easily between them.

FIG. 2 illustrates an optional suction shield 28 for use with the device of the present invention, which comprises a tube 30 having a distal end 32 and proximal end 34. The distal end 32 is closed and of hemispherical shape, having a plurality of ports 36 for communicating between the interior of a body cavity and the interior of the shield 28. The proximal end 34 of the shield 28 is open and connectable to the shield securing structure 16, so that when desired, the shield 28 may be attached to the shield securing structure 16. Use of the device with the shield 28 allows for the suctioning of large volumes of fluid without clogging or suctioning onto anatomical structures such as fallopian tubes or bowels. FIG. 3 illustrates the device of the invention with the shield 28 attached. In the preferred embodiment, the connecting means of the shield 28 is a set of male threads complementary to a corresponding set of female threads formed in the shield securing structure 16. In the preferred embodiment, the shield 28 is of sufficient length such that when attached to the shield securing structure 16, the distal end 32 of the shield 28 just clears the distal end 12 of the tube 10. Also in the preferred embodiment, the shield 28 is approximately 18 cm long, and has an internal diameter of 5 mm, although those skilled in the art will recognize that other lengths and diameters are possible. The shield 28 should also be made out of a corrosion-resistant material such as titanium.

Similar to the preferred embodiment of the tube 10, it is preferred that the shield ports 36 are arranged in uniform rows and columns, substantially similar to the arrangement of the tube ports 18. In the preferred embodiment, there are 8 columns spaced equidistantly apart, and 20 rows, each row being a known distance (such as 2.5 mm) apart, for allowing the shield 28 to be useful during endoscopic procedures as a ruler.

In use, the tube 10 can be connected via the valves 24 or 26 to sources of vacuum or irrigation, or both. The invention can also be used for aqua-dissection when it is connected to a source of irrigation. The rubber seal 20 can be removed and the end cap 22 added, so that a variety of other instruments can be inserted down through the tube 10 without causing further trauma to the patient, as that which would be caused by having to either remove the suction/irrigation device for inserting such other instruments into the same cannula as that which is used by the suction/irrigation device, or by having to create another incision for the emplacement of such other instruments. As long as the diameter of such other instruments is sufficiently smaller than the internal diameter of the tube 10 for allowing the flow of fluid between them and the interior surfaces of the tube 10, they may be inserted through the end cap 22 and into the tube 10 simultaneously with the use of suction and irrigation, since the end cap 22 with gasket prevents the loss of vacuum and/or irrigation fluid. The use of valves that are difficult to clog also will reduce the number of delays during operations. When large volumes of fluids need to be removed from the operative field, the tube 10 can be removed from the body, the shield 28 attached, the device reinserted and used to suction the fluids, without having to detach and attach a new instrument to the vacuum. Overall, the use of the invention will result in operations which take less time to perform, cause less trauma to the patient, and require less recovery time for the patient.

The inventor has given a non-limiting description of several embodiments of the present invention, to which many changes may be made without deviating from the spirit of the inherent inventive concept. While this invention has been described with reference to such illustrative embodiments, this description is not intended to be construed in a limiting sense. Various modifications and combinations of the various embodiments as well as other embodiments of this invention will be apparent to a person skilled in the art upon reference to this description. It is therefore contemplated that the appended claims cover any such modifications and/or embodiments that fall within the true scope of the present invention.

I claim:

1. An endoscopic device for use in medical procedures comprising:

a rigid hollow endoscopic tube having a distal end, a proximal end and a substantially cylindrical side wall, said distal end and said proximal end being open, and said endoscopic tube having an axis which is substantially straight, such that another endoscopic instrument having an external diameter smaller than the internal diameter of the endoscopic tube may be inserted therethrough while the distal end of the endoscopic tube is in a patient's body;

at least a port formed in the endoscopic tube side wall near said distal end means for transferring vacuum from a vacuum source to the endoscopic tube, and thereby effectuating the removal of fluids and debris from said patient's body while the endoscopic tube distal end is in said patient's body; and means for preventing the leakage of fluid or vacuum out of said proximal end.

2. The endoscopic device of claim 1, wherein the leakage preventing means includes means for providing a leak-proof fit between said proximal end and an endoscopic instrument inserted into the endoscopic tube through said proximal end.

3. The endoscopic device of claim 2, wherein said means for providing a leak-proof fit is an end cap attachable to said proximal end of said endoscopic tube, said end cap having an aperture therethrough for allowing the insertion of an endoscopic instrument therein and into the endoscopic tube while said tube distal end is inside a patient's body.

4. The endoscopic device of claim 1, further comprising,
a removable suction shield, comprising a hollow tube having an internal diameter which is larger than the external diameter of the endoscopic tube, an open shield proximal end for inserting the endoscopic tube therein, and a dome-shaped shield distal end; said shield further including a plurality of ports formed in the shield hollow tube and located near said shield distal end; and means for sealably securing the proximal end of said suction shield to the endoscopic tube when said tube is in the suction shield.

5. The endoscopic device of claim 4, wherein said securing means is a sealable shield securing structure circumscribing the endoscopic tube; and further wherein said shield and said shield securing structure are connectable via mutually complementary threads.

6. The endoscopic device of claim 4, wherein said plurality of shield ports are arranged uniformly for allowing a surgeon to measure distances when viewing the shield distal end.

7. The endoscopic device of claim 4, wherein the leakage preventing means includes means for providing a leak-proof fit between the endoscopic tube proximal end and a surgical instrument inserted into the endoscopic tube through said proximal end.

8. The endoscopic device of claim 1, wherein said at least a port is a plurality of ports arranged uniformly for allowing a surgeon to measure distances when viewing the endoscopic tube distal end.

9. The endoscopic device of claim 1, wherein the vacuum transferring means comprises a vacuum conduit in communication with the endoscopic tube interior and connected at a vacuum conduit first end to said endoscopic tube near said endoscopic tube proximal end; said vacuum conduit including a vacuum valve for regulating communication between the interior of the endoscopic tube and a source of vacuum which may be connected to a second end of said vacuum conduit.

10. The endoscopic device of claim 1, wherein the leakage preventing means is a removable seal.

11. The endoscopic device of claim 1, further including means for transferring irrigation fluid from an irrigation source to the endoscopic tube, and thereby effectuating irrigation of a surgical site inside said patient's body while the distal end of the endoscopic tube is in said patient's body.

12. The endoscopic device of claim 11, wherein the irrigation fluid transferring means comprises an irrigation conduit in communication with the endoscopic tube interior and connected at an irrigation conduit first end to said endoscopic tube near said tube proximal end; said irrigation conduit including an irrigation valve for regulating communication between the endoscopic tube interior and a source of irrigation which may be connected to a second end of said irrigation conduit.

13. An endoscopic device for use in medical procedures comprising:
a rigid hollow endoscopic tube having a distal end, a proximal end and a substantially cylindrical side wall, said distal end and said proximal end being open, and said endoscopic tube having an axis which is substantially straight, such that another endoscopic instrument having an external diameter smaller than the internal diameter of the endoscopic tube may be inserted therethrough while the distal end of the endoscopic tube is in a patient's body;

a plurality of ports formed in the endoscopic tube side wall near said distal end;

means for transferring irrigation fluid from an irrigation source to the endoscopic tube, and thereby effectuating irrigation of a surgical site inside said patient's body while the distal end of the endoscopic tube is in said patient's body; and means for preventing the leakage of fluid or vacuum out of said proximal end.

14. The endoscopic device of claim 13, wherein the irrigation fluid transferring means comprises an irrigation conduit in communication with the endoscopic tube interior and connected at an irrigation conduit first end to said endoscopic tube near said tube proximal end; said irrigation conduit including an irrigation valve for regulating communication between the endoscopic tube interior and a source of irrigation which may be connected to a second end of said irrigation conduit.

15. The endoscopic device of claim 13, further including means for transferring vacuum from a vacuum source to the endoscopic tube, and thereby effectuating the removal of fluids and debris from said patient's body while the endoscopic tube distal end is in said patient's body.

16. The endoscopic device of claim 15, wherein the vacuum transferring means comprises a vacuum conduit in communication with the endoscopic tube interior and connected at a vacuum conduit first end to said endoscopic tube near said endoscopic tube proximal end; said vacuum conduit including a vacuum valve for regulating communication between the interior of the endoscopic tube and a source of vacuum which may be connected to a second end of said vacuum conduit.

17. The endoscopic device of claim 13, further comprising,
a removable suction shield, comprising a hollow tube having an internal diameter which is larger than the external diameter of the endoscopic tube, an open shield proximal end for inserting the endoscopic tube therein, and a dome-shaped shield distal end; said shield further including a plurality of ports formed in the shield hollow tube and located near said shield distal end; and means for sealably securing the proximal end of said suction shield to the endoscopic tube when said tube is in the suction shield.

18. An endoscopic device for use in medical procedures comprising:
a rigid hollow endoscopic tube having a distal end, a proximal end and a substantially cylindrical side wall, said distal end and said proximal end being open, and said endoscopic tube having an axis which is substantially straight, such that another endoscopic instrument having an external diameter smaller than the internal diameter of the endoscopic tube may be inserted therethrough while the distal end of the endoscopic tube is in a patient's body;

a plurality of ports formed in the endoscopic tube side wall near said distal end;

means for transferring vacuum from a vacuum source to the endoscopic tube, and thereby effectuating the removal of fluids and debris from said patient's body while the endoscopic tube distal end is in said patient's body;

means for transferring irrigation fluid from an irrigation source to the endoscopic tube, and thereby effectuating irrigation of a surgical site inside said patient's body while the distal end of the endoscopic tube is in said patient's body; and means for preventing the leakage of fluid or vacuum out of said proximal end.

19. The endoscopic device of claim 18, further comprising, a removable suction shield, comprising a hollow tube having an internal diameter which is larger than the external diameter of the endoscopic tube, an open shield proximal end for inserting the endoscopic tube therein, and a dome-shaped shield distal end; said shield further including a plurality of ports formed in the shield hollow tube and located near said shield distal end; and means for sealably securing the proximal end of said suction shield to the endoscopic tube when said tube is in the suction shield.

* * * * *